United States Patent
Pawlak, II

(10) Patent No.: US 10,091,995 B2
(45) Date of Patent: Oct. 9, 2018

(54) GIBBERELLIN FORMULATIONS

(71) Applicant: Valent U.S.A., Corporation, Walnut Creek, CA (US)

(72) Inventor: John Andrew Pawlak, II, Walnut Creek, CA (US)

(73) Assignee: VALENT U.S.A., CORPORATION, Walnut Creek, CA (US)

(*) Notice: Subject to any disclaimer, the term of this patent is extended or adjusted under 35 U.S.C. 154(b) by 0 days.

(21) Appl. No.: 15/177,471

(22) Filed: Jun. 9, 2016

(65) Prior Publication Data

US 2016/0360748 A1 Dec. 15, 2016

Related U.S. Application Data

(60) Provisional application No. 62/172,875, filed on Jun. 9, 2015.

(51) Int. Cl.
*A01N 43/12* (2006.01)
*A01N 25/02* (2006.01)
*A01N 25/22* (2006.01)
*A01N 25/30* (2006.01)

(52) U.S. Cl.
CPC ............. *A01N 43/12* (2013.01); *A01N 25/02* (2013.01); *A01N 25/22* (2013.01); *A01N 25/30* (2013.01)

(58) Field of Classification Search
CPC combination set(s) only.
See application file for complete search history.

(56) References Cited

U.S. PATENT DOCUMENTS

| | | |
|---|---|---|
| 4,936,901 A | 6/1990 | Surgant, Sr. et al. |
| 5,622,658 A | 4/1997 | Lloyd et al. |
| 2005/0198896 A1 | 9/2005 | Quaghebeur |
| 2014/0128261 A1 | 5/2014 | Etheridge et al. |
| 2014/0221207 A1 | 8/2014 | Asolkar et al. |

FOREIGN PATENT DOCUMENTS

EP   0 252 897   1/1988

OTHER PUBLICATIONS

INDUCE® label, Helena Holding Co., 2005.*
International Search Report and Written Opinion issued by the International Bureau in corresponding application No. PCT/US2016/036557 dated Sep. 1, 2016.

* cited by examiner

*Primary Examiner* — John Pak
(74) *Attorney, Agent, or Firm* — Wood, Phillips, Katz, Clark & Mortimer

(57) ABSTRACT

The present invention relates to gibberellin formulations and methods of their use. Specifically, formulations of the present invention are directed toward agricultural formulations including gibberellin and an adjuvant, wherein the ratio of gibberellin to adjuvant is from about 1:0.005 to about 1:0.5, the adjuvant contains from about 85 to about 95% of a blend of alkyl aryl polyoxyalkane ethers, dimethylsiloxane, and free fatty acids, the formulation does not include isopropyl alcohol, propylene glycol, or a polysorbate surfactant, and the ratios are expressed in percentage weight of the gibberellin to volume of the adjuvant.

2 Claims, No Drawings

GIBBERELLIN FORMULATIONS

CROSS REFERENCE TO RELATED APPLICATIONS

This application is a Non-Provisional application which claims the benefit of U.S. Provisional Application No. 62/172,875 filed Jun. 9, 2015, the disclosure of which is incorporated herein by reference.

FIELD OF THE INVENTION

The present invention relates to storage stable gibberellin formulations.

BACKGROUND OF THE INVENTION

Gibberellins are a class of plant growth regulators which are diterpenoid acids. Gibberellins are commercially produced by fermentation of a natural fungus, *Gibberella fugikuroi*. Gibberellins are marketed under various trade names and are commercially used on a variety of fruit orchards, vegetable crops, row crops, and ornamental crops. The predominantly used gibberellin is gibberellin acid ("$GA_3$").

Gibberellins have been formulated in numerous ways over the years in order to attempt to overcome their low solubility. For example, gibberellins have been formulated as solutions, soluble powders, wettable powders, tablets, and water-dispersible granules. The disadvantages of each category of the prior art formulations are discussed below.

Solution formulations of the prior art are disadvantageous in several respects. The formulations are less concentrated due to low solubility of gibberellins, have limited storage stability, and/or contain unacceptable amounts of volatile organic compounds ("VOCs").

The low solubility of $GA_3$, gibberellin$_4$ ("$GA_4$"), or gibberellin$_{4/7}$ ("$GA_{4/7}$") in some solvents, such as propylene glycol, does not permit preparation of high concentration solution formulations. These low strength solution formulations require larger packaging, more storage space, and higher associated transportation, warehousing, and container disposal costs. Due to very low solubility and undesirable hydrolysis, it has been especially difficult to formulate $GA_3$ in aqueous systems.

In order to overcome solubility issues, some formulations use solvents with amounts of VOCs that are not safe for the environment. For example, isopropyl alcohol and methyl alcohol offer severe disadvantages such as flammability and toxicity, which lead to restrictions in manufacturing, packaging, labeling, transportation, and warehousing of such solutions. Tetrahydrofurfuryl alcohol ("THFA") is considered corrosive to the eye and skin.

One way to overcome the solubility issues with $GA_3$, $GA_4$, and $GA_{4/7}$ is to prepare soluble powder formulations. These powder formulations dissolve readily when mixed with water and form true solutions. Once the solution is formed, no further mixing or agitation of the tank-mix is required.

Another way to overcome the solubility issues is to create a wettable powder. A wettable powder formulation is a dry, finely ground formulation. In this type of formulation, the active ingredient is combined with a finely ground dry carrier, usually a mineral clay, along with other ingredients that enhance the ability of the powder to be suspended in water. Upon mixing the wettable powder with water, a suspension is formed, which is then applied by a spray technique. Often the spray liquid must be continuously mixed to prevent settling of insoluble compositions.

However, wettable powders and soluble powder formulations tend to produce dust upon handling, such as when pouring, transferring or measuring them. This dust may pose health hazards. Further, powder formulations tend to wet poorly and also solubilize slowly upon addition to water. Powder formulations thus take longer to wet, disperse and solubilize in a tank-mix. Formation of lumps or partially solubilized spray solutions will lead to uneven distribution of the plant growth regulator in the tank-mix with the potential for reduced field performance. Sometimes, foam in the spray tank caused by spray tank adjuvants can also affect wetting and solubility of wettable and soluble powders. Wettable powder formulations will also leave undesirable insoluble residues both in the tank and on the sprayed foliage and fruit.

Another type of agricultural formulation is a tablet. Tablet formulations are pre-measured dosage delivery systems. They are useful in small areas, or for ornamental purposes. Tablet formulations may be effervescent, which dissolve in water over a period of two to ten minutes depending upon the type and size of the tablet. However, tablets generally deliver only between 0.1 to 1 gram of active ingredient per tablet. They are not ideal for large-scale field operations. Moreover, effervescent tablets are highly susceptible to humidity and may be slow to dissolve and are expensive.

Yet another type of agricultural formulation is a water-dispersible granule. Water-dispersible granules are also known as wettable granules or dry flowables. This type of formulation is similar to a wettable powder, except that the active ingredient is formulated as a dispersible granule. To prepare the water-dispersible granules for spray application, they are dispersed in water and form a suspension upon agitation. Many different water-dispersible granular formulations are known for agricultural chemicals. For example, EP 0 252 897 and U.S. Pat. No. 4,936,901 disclose encapsulated plant growth regulators in water dispersible granular formulations; and U.S. Pat. No. 5,622,658 discloses an extrudable composition for preparing water-dispersible granules.

Water-dispersible granules usually have no greater than eight percent moisture content, and form suspensions when added to aqueous solutions. The resulting suspension must be agitated for a period of time in order to fully disperse it. Agitation or by-pass recirculation of the tank-mix must also be maintained during application. The quality of water-dispersible granules is highly process- and active-ingredient-dependent; and can result in low yield recoveries, poor attrition resistance leading to dust potential, high manufacturing cost and poor dispersion. Generally, sprays of dissolved water-dispersible granular formulations leave undesirable insoluble residues on the treated foliage and fruit.

For $GA_3$, $GA_4$, and $GA_{4/7}$ formulations to be efficacious, the active ingredient must solubilize in tank-mixes prior to application. Otherwise, product efficacy will be severely affected. When water-dispersible granules are used, the grower often may not realize if he has achieved complete solubility of the active ingredient in the spray solutions. In addition, water-dispersible granules can harden over time and thus result in poor dispersibility and solubility of the active ingredient. Dust and caking may be problems with certain water-dispersible granules and powder formulations.

Therefore, there is a need for environmentally safe, non-phytotoxic, efficacious, high strength gibberellin solution formulations. The improved formulations should overcome the toxicity, handling, storage, transportation, and solubility issues encountered by prior art formulations.

SUMMARY OF THE INVENTION

In one aspect, the present invention is directed to liquid agricultural formulations containing a gibberellin and an adjuvant, wherein the ratio of gibberellin to adjuvant is from about 1:0.005 to about 1:0.5, the adjuvant contains from about 85 to about 95% of a blend of alkyl aryl polyoxyalkane ethers, dimethylsiloxane, and free fatty acids, the formulation does not include isopropyl alcohol, propylene glycol, or a polysorbate surfactant, and the ratios are expressed in percentage weight of the gibberellin to volume of the adjuvant.

In another aspect, the invention is directed to methods for regulating plant growth comprising the step of treating soil or a plant with an effective amount of the formulations of the present invention.

DETAILED DESCRIPTION OF THE INVENTION

Despite gibberellins' known stability issues, Applicant has unexpectedly discovered that formulations containing about 1:0.005 to about 1:0.5 (weight to volume) of a gibberellin to nonionic adjuvant containing a blend of alkyl aryl polyoxyalkane ethers, dimethylsiloxane, and free fatty acids, resulted in a storage stable formulation (see, for example, Examples 1 and 2). Applicant's formulations are also non-phytotoxic while being efficacious.

Alkyl aryl polyoxyalkane ethers (or alkyl aryl polyoxyalkene ethers) are liquid emulsifiers. Examples of alkyl aryl polyoxyalkane ethers include nonyl phenol ethoxylate or octyl phenol ethoxylate.

Dimethylsiloxanes are defoamer surfactants. Examples of dimethylsiloxane defoamers can be found in, for example, McCutcheon's volume 2: Functional Materials, North American Edition, 2013, pages 80 to 94.

Free fatty acids (or short chain fatty acid or volatile fatty acids) are fatty acids with a carbon chain of six carbons or fewer. Examples of free fatty acids include formic acid, acetic acid, propanoic acid, isobutyric acid (2-methylpropanoic acid), butyric acid, isovaleric acid (3-methylbutanoic acid), and valeric acid (pentanoic acid).

In an embodiment, the invention is directed to liquid agricultural formulations comprising a gibberellin and an adjuvant, wherein the ratio of gibberellin to adjuvant is from about 1:0.005 to about 1:0.5, the adjuvant contains from about 85 to about 95% of a blend of alkyl aryl polyoxyalkane ethers, dimethylsiloxane, and free fatty acids, the formulation does not include isopropyl alcohol, propylene glycol, or a polysorbate surfactant, and the ratios are expressed in percentage weight of the gibberellin to volume of the adjuvant.

In a preferred embodiment, the gibberellin in the formulations of the present invention is $GA_3$, $GA_4$, or $GA_{4/7}$. In a more preferred embodiment, the gibberellin is $GA_3$.

In another embodiment, the formulations of present invention include gibberellin and the adjuvant in a ratio of from about 1:0.01 to about 1:0.1 weight to volume. In a preferred embodiment, the formulations contain gibberellin and the adjuvant in a ratio of about 1:0.05 weight to volume.

In another embodiment, the adjuvant contains from about 87 to about 92% of a blend of alkyl aryl polyoxyalkane ethers, dimethylsiloxane, and free fatty acids. In a preferred embodiment, the adjuvant contains from about 89 to about 91% of a blend of alkyl aryl polyoxyalkane ethers, dimethylsiloxane, and free fatty acids. In a more preferred embodiment, the adjuvant contains about 90% of a blend of alkyl aryl polyoxyalkane ethers, dimethylsiloxane, and free fatty acids.

In a further embodiment, the formulations of present invention contain from about 0.01% to about 5% v/v nonionic surfactant. In a preferred embodiment, the formulations contain from about 0.01% to about 2% v/v nonionic surfactant. In a more preferred embodiment, the formulations contain from about 0.1% to about 1% v/v nonionic surfactant. In a most preferred embodiment, the formulations about 0.25% v/v nonionic surfactant.

In yet another embodiment, the formulations of present invention contain from about 0.1 to about 50% v/v gibberellin. In a preferred embodiment, the formulations contain from about 1 to about 20% v/v gibberellin. In a more preferred embodiment, the formulations contain from about 1 to about 10% v/v gibberellin. In a most preferred embodiment, the formulations contain about 3% v/v gibberellin.

In yet another embodiment, the formulations of present invention include from about 0.001 to about 20 grams per milliliter of gibberellin. In a preferred embodiment, the formulations contain from about 0.001 to about 10 grams per milliliter of gibberellin. In a more preferred embodiment, the formulations contain from about 0.01 to about 0.05 grams per milliliter of gibberellin. In a most preferred embodiment, the formulations contain about 0.02 grams per milliliter of gibberellin.

In a preferred embodiment, about 3 grams of gibberellin and about 0.0025 gallons of liquid adjuvant (0.1514 milliliters) are added to about 10 gallons of water. Preferably, this mixture (pre-mix) is added to a tank mixer.

In another preferred embodiment, about 3 grams of $GA_3$ and about 0.0025 gallons of liquid adjuvant (0.1514 milliliters) are added to about 10 gallons of water. Preferably, this mixture (pre-mix) is added to a tank mixer. Preferably, the contents of the tank mixer are used to treat 1 acre of land.

The formulations of the present invention are also low VOC formulations. This means that the formulations contain less than or equal to 25% emission potential, as determined by thermo gravimetric analysis ("TGA"). Gibberellin formulations with greater than 25% emission potential, as determined by TGA, are considered High-VOC products by CADPR (California Department of Pesticide Regulation). TGA involves heating a pesticide sample in an environmentally controlled chamber while the rate of sample mass loss is measured. CADPR states that the emission potential of a pesticide formulation is determined by taking the mean of three replicate TGA measurements of the pesticide(s) and then subtracting the percent water and the exempt compounds from the measurement. The TGA process is well known by those of skill in the art.

In a further embodiment, the present invention is directed to methods for regulating plant growth comprising treating a soil or a plant with an effective amount of a formulation of the present invention.

In a further embodiment, the formulations of present invention are applied to the plants at a rate of from about 0.1 to about 50 grams of gibberellin per acre. In a preferred embodiment, the formulations are applied to the plants at a rate of from about 1 to about 20 grams of gibberellin per acre. In a more preferred embodiment, the formulations are applied to the plants at a rate of from about 1 to about 10 grams of gibberellin per acre. In a most preferred embodiment, the formulations are applied to the plants at a rate of about 3 grams per acre.

Formulations of the present invention may be used as a pre-mixture product. The pre-mixture product can be added to a tank mixer prior to application to the plants. The use of the pre-mixture formulations allows for an easier mixing process for the end user.

Formulations of the present invention may be used on any plant in need of gibberellin treatment, for example, on: artichokes to accelerate maturity and increase yield; blueberries to improve fruit set and fruit size; bananas to stimulate plant growth and reduce effects of stress, or post-harvest for maintaining fruit quality; carrots to maintain foliage growth during periods of stress; celery to increase plant height and yield; cherries to increase fruit size, firmness and quality or to delay maturity for a more orderly harvest; citrus to increase fruit set and yield, to delay rind aging, reduce physiological disorders, or delay maturity for a more orderly harvest; collard greens to facilitate harvest, increase yield, and improve quality; cotton to promote early season growth and increase seedling vigor; and cucumbers to stimulate fruit set during periods of cool weather; pasture land used for animal grazing; and corn. The formulations can be used post harvest on bananas and citrus, etc. Formulations of the present invention could also be used on grapes, melons, pecans, peppers, pineapples, rice, rhubarb, spinach, stone fruits, strawberries, watercress and other plants in need of treatment.

The disclosed embodiments are simply exemplary embodiments of the inventive concepts disclosed herein and should not be considered as limiting, unless the claims expressly state otherwise.

The present invention is also directed to methods of regulating plant growth comprising the step of treating soil or a plant with an effective amount of the formulations described above. The formulation may be diluted with water and spray-applied. For example, when the plant is a fruit-producing plant, such as a grape plant, a grape-producing plant so treated produces larger grapes and/or grapes having higher percentage of soluble solids.

The term "effective amount" means the amount of the formulation that will provide the desired effect on the plant that is being treated. The "effective amount" will vary depending on the formulation concentration, the type of plants(s) being treated, and the result desired, among other factors. Thus, it is not always possible to specify an exact "effective amount." However, an appropriate "effective amount" in any individual case may be determined by one of ordinary skill in the art. For example, effective amounts of formulations of the present invention may be from about 0.1 to about 50% of gibberellin, and more preferably from about 1% to about 20% gibberellin or from about 1% to about 10% gibberellin.

Other components of the formulation may be included in nominal amounts that do not affect the storage stability characteristics of the present formulations. Additional components include surface active agents, crystal growth inhibitors, stickers, spreaders, leaf penetrants, dispersants, systemic acquired resistance inducers, systemic acquired resistance inhibiters, anti-foaming agents, preservatives, pH regulators, cosolvents, humectants, dyes, UV protectants, vehicles, sequestrants or other components which facilitate production, storage stability, product handling and application.

It is also contemplated that the ready-to-mix composition materials of this invention may be used in combination with other active ingredients, such as herbicides, fungicides, insecticides, bactericides, nematicides, biochemical pesticides, plant produced pesticides (botanicals), safeners or plant nutrients.

As used herein, the term "herbicide" broadly refers to compounds or compositions that are used as herbicides, as well as herbicide safeners and algicides. Herbicides may include, but are not limited to, 1,2,4-triazinones, 1,3,5-triazines, alkanamides (acetamides), anilides, aryloxyalkanoic acids, aryloxyphenoxypropionates, benzamides, benzamides (L), benzenedicarboxylic acids, benzofurans, benzoic acids (auxins), benzonitriles, benzothiadiazinones, benzothiazolones, carbamates (DHP), carbamates, chloroacetamides, cyclohexanedione oximes, dinitroanilines, dinitrophenols, diphenyl ethers, diphenyl ethers (cbi), glycine derivatives, halogenated alkanoic acids, hydroxybenzonitriles, imidazolinones, isoxazoles, isoxazolidinones, N-phenylphthalimides, organoarsenics, oxadiazoles, oxazolidinediones, oxyacetamides, phenoxycarboxylic acids, phenyl carbamate herbicides, phenylpyrazole herbicides, phenylpyridazines, phosphinic acids, phosphorodithioates, phthalamates, pyrazole herbicides, pyridazines, pyridazinones (PDS), pyridazinones (PSII), pyridines, pyridinecarboxamides, pyridinecarboxylic acids, pyrimidindiones, pyrimidines, pyrimidinyl-oxybenzoics, pyrimidinyloxybenzoic analogs, quinolinecarboxylic acids, BI class and IV including thiocarbamate, semi-carbazones, sulfonylaminocarbonyl-triazolinones, sulfonylureas, tetrazolinones, thiadiazoles, thiocarbamates, triazoles, triazolinones, triazolopyrimidines, triketones, uracils, ureas, 2,3,6-TBA, 2,4,5-T, 2,4-D, 2,4-D-2-ethylhexyl, 2,4-DB, 2,4-D-dimethylammonium, 2,4-D-isopropyl, 2,4-D-isopropyl, 2,4-D-trolamine (2,4-D-triethanolamine), ACD 10614, ACD 10435, acetochlor, acifluorfen, acifluorfen-sodium, aclonifen, acrolein, AD 67, alachlor, alloxydim-sodium, ametryn, amicarbazone, amidosulfuron, amitrole, ammonium sulfamate, anilofos, asulam, atraton, atrazine, azafenidin, azimsulfuron, aziprotryne, barban, beflubutamid, benazolin, benazolin-ethyl, benfluralin, benfuresate, benoxacor, bensulfuron-methyl, bensulide, bentazone, benzobicyclon, benzofenap, benzoylprop, enzoylprop-ethyl, bifenox, bilanafos-sodium, bispyribac-sodium, borax, bromacil, bromobutide, bromofenoxim, bromoxynil, bromoxynil octanoate, bromoxynil-potassium, brompyrazon, butachlor, butafenacil, butenachlor, buthidazole, butralin, butroxydim, buturon, cafenstrole, calcium cyanamide, carbetamide, carfentrazone-ethyl, chlomethoxyfen, chloramben, chlorbromuron, chlorbufam, chlorfenac, chlorfenac-sodium, chlorfenprop, chlorfenprop-methyl, chlorfenprop, chlorfenprop-ethyl, chlorflurenol-methyl, chloridazon, chlorimuron-ethyl, chlornitrofen, chloroacetic acid, chloro-toluron, chloroxuron, chlorpropham, chlorsulfuron, chlorthal-dimethyl, chlorthiamid, cinidon-ethyl, cinosulfuron, clethodim, sethoxydim, tepraloxydim, tralkoxydim, clodinafop-propargyl, clofop, clofop-isobutyl, clomazone, clomeprop, clopyralid, cloquintocet-mexyl, cloransulam-methyl, credazine, cumyluron, cyanamide, cyanazine, cyclosulfamuron, cycloxydim, cycluron, cyhalofop-butyl, cyometrinil, daimuron, dazomet, desmedipham, desmetryn, di-allate, dicamba, dichlobenil, dichlormid, dichlorprop, dichlorprop-isoctyl, dichlorprop-P, diclofop, diclofop-methyl, diclosulam, diethatyl-ethyl; diethatyl, difenoxuron, difenzoquat metilsulfate, diflufenican, diflufenzopyr, dikegulac, dikegulac-sodium, dimefuron, dimepiperate, dimethachlor, dimethametryn, dimethipin, dimethylarsinic acid, dinitramine dinoseb, dinoseb acetate, dinoterb, diphenamid, dipropetryn, disul, disul-sodium, dithiopyr, diuron, DNOC, DSMA, eglinazine-ethyl, eglinazine, EL 177, endothal, ethalfluralin, ethametsulfuronmethyl, ethidimuron, ethofumesate, ethoxysulfuron, etobenzanid, fenchlorazole-ethyl, fenclorim, fenoprop, fenopropbutotyl, fenoxaprop-ethyl, fenoxaprop, fenoxaprop-P, fenoxaprop-P-ethyl, fenthiaprop, fenthiaprop-ethyl, fentrazamide, fenuron, flamprop-methyl, flamprop-isopropyl, flamprop, flamprop-M-isopropyl, flamprop-M-methyl, flazasulfuron, florasulam, fluazifop-butyl, fluazifop-P, fluazifop-P-butyl, fluazolate, flucarbazone-sodium, fluchloralin, flufenacet, flumetsulam, flumiclorac-pentyl, flumioxazin, flumipropyn, fluometuron, fluorodifen, fluoroglycofen-ethyl, fluothiuron, flupoxam, flupropanate-sodium, flupyrsulfuron-methyl-sodium, flurazole, flurenol-butyl, fluridone, flurochloridone, fluroxypyr, fluroxypyr-meptyl, flurtamone, fluthiacet-methyl, fomesafen, foramsulfuron, fosamine-ammonium, furilazole, glufosinate-ammonium, glyphosate, glyphosate-ammonium, glyphosate-isopropylammonium, glyphosate-sodium, glyphosate-trimesium, halosulfuron-methyl, haloxyfop, haloxyfop-etotyl, haloxyfop-P, hexaflurate, hexazinone, imazamethabenzmethyl, imazamox, imazapic, imazapyr, imazapyr-isopropylammonium, imazaquin, imazethapyr, imazosulfuron, indanofan, iodosulfuron-methyl-sodium, ioxynil, ioxynil octanoate, ioxynil-sodium, isocarbamid, isocil, isomethiozin, isonoruron, isoproturon, isouron, isoxaben, isoxaflutole, isoxapyrifop, karbutilate, lactofen, lenacil, linuron, LS830556, maleic hydrazide, MCPA, MCPA-thioethyl, MCPB, MCPB-ethyl, mecoprop, mecoprop-P, medinoterb acetate, medinoterb, mefenacet, mefenpyrdiethyl, mefluidide, mesosulfuron-methyl, mesotrione, metamifop, metamitron, metazachlor, methabenzthiazuron, methazole, methiuron, methoprotryne, methoxyphenone, methyl isothiocyanate, methylarsonic acid, methyldymron, metobenzuron, metobromuron, metolachlor, metosulam, metoxuron, metribuzin, metsulfuron-, ethyl, MK-616, monalide, monolinuron, monuron, monuron-TCA, MSMA, naphthalic anhydride, naproanilide, napropamide, naptalam, NC-330, neburon, nicosulfuron, nitralin, nitrofen, nonanoic acid, norflurazon, oleic acid (fatty acids), orbencarb, oryzalin, oxabetrinil, oxadiargyl, oxadiazon, oxasulfuron, oxaziclomefone, oxyfluorfen, pendimethalin, penoxsulam, pentachlorophenol, pentanochlor, pentoxazone, perfluidone, pethoxamid, phenisopham, phenmedipham, phenylmercury acetate, picolinafen, primisulfuron-methyl, prodiamine, profluralin, proglinazine-ethyl, proglinazine, prometon, prometryn, propachlor, propanil, propaquizafop, propazine, propham, propisochlor, propoxycarbazone-sodium, propyzamide, prosulfuron, pyraflufen-ethyl, pyrazolynate, pyrazosulfuron-ethyl, pyrazoxyfen, pyribenzoxim, pyributicarb, pyridate, pyriftalid, pyriminobac-methyl, pyrithiobac-sodium, quinclorac, quinmerac, quinoclamine, quizalofop-ethyl, quizalofop-P-ethyl, quizalofop-P-tefuryl, rimsulfuron, sebuthylazine, secbumeton, siduron, simazine, simetryn, S-metolachlor, SMY 1500, sodium chlorate, sulcotrione, sulfentrazone, sulfometuron-methyl, sulfosulfuron, tebuthiuron, tepraloxydim, terbacil, terbumeton, terbuthylazine, terbutryn, thenylchlor, thiazafluron, thiazopyr, thidiazimin, thifensulfuron-methyl, thiobencarb, 1-dichloroacetylazepane, tralkoxydim, tri-allat, triasulfuron, tribenuron-methyl, trichloroacetic acid, triclopyr, tridiphane, trietazine, trifloxysulfuron-sodium, trifluralin, and triflusulfuron-methyl. In a preferred embodiment, the herbicide is selected from the group consisting of clethodim, sethoxydim, tepraloxydim, and tralkoxydim. In a more preferred embodiment, the herbicide is clethodim.

Fungicides may include, but are not limited to, amino acid amide carbamates, anilinopyrimidines, antibiotics, aromatic hydrocarbons, heteroaromatics, chloro/nitrophenyls, benzamides (F), benzenesulfonamides, benzimidazoles, benzimidazole precursors, benzotriazines, carboxamides, cinnamic acids, cyanoacetamide oximes, dicarboximides, dithiolanes, DMI: imidazoles, piperazines, pyrimidines, and triazoles; enopyranuronic acid antibiotics, heteroaromatic hydroxyanilides, MBI: dehydratases and reductases; morpholine morpholines, morpholine spiroketalamines, multi-site chloronitriles, multi-site dimethyldithiocarbamates, multi-site guanidines, multi-site inorganics, multi-site phthalimides, multi-site quinones, multi-site sulfamides, N-phenyl carbamate fungicides, organotin fungicides, phenylamide: acylalanines, phenylamide: butyrolactones, phenylamide: oxazolidinones, phenylpyrroles, phenylurea fungicides, phosphonates, phosphorothiolates, pyridazinone fungicides, pyrimidinamines, pyrimidinols, QiI, quinolines, SBI class IV: thiocarbamates, strobilurin analog: dihydrodioxazines, strobilurin type: imidazolinones, strobilurin type: methoxyacrylates, strobilurin type: ethoxycarbamates, strobilurin type: oxazolidinediones, strobilurin type: oximinoacetamides, strobilurin type: oximinoacetates, thiazolecarboxamides, thiocarbamate fungicides, and thiophenecarboxamides. Suitable fungicides include 1,2-dichloro-propane, 2-methoxyethylmercury chloride, 2-phenylphenol, 8-hydroxy-quinoline sulfate, ampropylfos, anilazine, azaconazole, azoxystrobin, benalaxyl, benodanil, benomyl, benquinox, benthiavalicarb-isopropyl, binapacryl, biphenyl, bis (tributyltin) oxide, bitertanol, blasticidin-S, borax, boscalid, bromuconazole, bupirimate, buthiobate, captafol, captan, carbendazim, carboxin, carpropamid, CGA 80 000, chinomethionat, chlobenthiazone, chloraniformethan, chloroneb, chlorothalonil, chlozolinate, climbazole, copper oxychloride, copper sulfate, copper sulfate (tribasic), cuprous oxide, cyazofamid, cyflufenamid, cymoxanil, cyproconazole, cyprodinil, cyprofuram, dazomet, dichlofluanid, dichlone, dichlorophen, diclobutrazol, diclocymet, diclomezine, dicloran, diethofencarb, difenoconazole, difenzoquat metilsulfate, diflumetorim, dimethirimol, dimethomorph, dimoxystrobin, diniconazole, dinobuton, dinocap, diphenylamine, ditalimfos, dithianon, dodemorph, dodemorph acetate, dodine, drazoxolon, edifenphos, epoxiconazole, etaconazole, etem, ethaboxam, ethirimol, etridiazole, famoxadone, fenamidone, fenarimol, fenbuconazole, fenfuram, fenhexamid, fenitropan, fenoxanil, fenpiclonil, fenpropimorph, fentin acetate, fentin hydroxide, ferimzone, fluazinam, fludioxonil, flumorph, fluoroimide, fluotriazole, fluoxastrobin, fluquinconazole, flusilazole, flusulfamide, flutolanil, flutriafol, folpet, fosetyl-aluminum, fuberidazole, furalaxyl, furametpyr, furconazole-cis, furmecyclox, glyodin, griseofulvin, halacrinate, hexachlorobenzene, hexaconazole, hymexazol, imazalil, imibenconazole, iminoctadine triacetate, iminoctadine tris(albesilate), ipconazole, iprodione, iprovalicarb, isoprothiolane, kasugamycin hydrochloride hydrate, kresoxim-methyl, mebenil, mepanipyrim, mepronil, mercuric chloride, metalaxyl, metalaxyl-M, metconazole, methasulfocarb, methfuroxam, methyl iodide, methyl isothiocyanate, metominostrobin, metsulfovax, mildiomycin, myclobutanil, myclozolin, natamycin, nitrothal-isopropyl, nuarimol, ofurace, oleic acid, fatty acids), oxabetrinil, oxadixyl, oxpoconazole fumarate, oxycarboxin, penconazole, pencycuron, pentachlorophenol, phenylmercury acetate, phenylmercury dimethyldithiocarbamate, phenylmercury nitrate, phosphonic acid, phthalide, picoxystrobin, polyoxin B, polyoxorim, potassium bicarbonate, potassium hydroxyquinoline sulfate, prochloraz, procymidone, propamocarb hydrochloride, propiconazole, proquinazid, prothiocarb; prothiocarb hydrochloride, prothioconazole, pyracarbolid, pyraclostrobin, pyrazophos, pyributicarb, pyrimethanil, pyroquilon, quinoclamine, quinoxyfen, quintozene, silthiofam, simeconazole, sodium bicarbonate, spiroxamine, SSF-109, sulfur, tebuconazole, tecnazene, tetraconazole, thiabendazole, thicyofen, thifluzamide, thiophanate, thiophanate-methyl, thiram, tiadinil, tolclofos-methyl, tolylfluanid, triadimefon, triadimenol, triamiphos, triazoxide, trichlamide, tricyclazole, trifloxystrobin, triflumizole, triforine, triticonazole, urbacid, validamycin, vinclozolin, zarilamid, ziram, and zoxamide.

Bactericides may include, but are not limited to, bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.

Insecticides, acaricides and nematicides may include, but are not limited to, abamectin, ABG-9008, acephate, acequinocyl, acetamiprid, acetoprole, acrinathrin, AKD-1022, AKD-3059, AKD-3088, alanycarb, aldicarb, aldoxycarb, allethrin, alpha-cypermethrin (alphamethrin), amidoflumet, aminocarb, amitraz, avermectin, AZ-60541, azadirachtin, azamethiphos, azinphos-methyl, azinphos-ethyl, azocyclotin, *Bacillus firmus, Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, *Bacillus thuringiensis israelensis*, baculoviruses, *Beauveria bassiana, Beauveria tenella*, benclothiaz, bendiocarb, benfuracarb, bensultap, benzoximate, beta-cyfluthrin, beta-cypermethrin, bifenazate, bifenthrin, binapacryl, bioallethrin, bioallethrin-S-cyclopentyl isomer, bioethanomethrin, biopermethrin, bioresmethrin, bistrifluoron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, chinomethionat, chlorantraniliprole, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cisresmethrin, cis-permethrin, clocythrin, cloethocarb, clofentezine, clothianidin, clothiazoben, codlemone, coumaphos, cyanofenphos, cyanophos, cyantraniliprole, cycloprene, cycloprothrin, cyfluthrin, cyflumetofen, cyhalothrin, cyhexatin, cypermethrin, cyphenothrin (1R-trans-isomer), cyromazine, DDT, deltamethrin, demeton-S-methyl, demeton-S-methylsulfone, diafenthiuron, dialifos, diazinon, dichlofenthion, dichlorvos, dicofol, dicrotophos, dicyclanil, diflubenzuron, dimefluthrin, dimethoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethion, ethiprole, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubendiamide, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-cyhalothrin, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, *Metharhizium anisopliae, Metharhizium flavoviride*, methidathion, methiocarb, methomyl, methoprene, methoxychlor, methoxyfenozide, metofluthrin, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl, *Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, potassium oleate, prallethrin, profenofos, profluthrin, promecarb, propaphos, propargite, propetamphos, propoxur, prothiofos, prothoate, protrifenbute, pymetrozine, pyraclofos, pyrafluprole, pyresmethrin, pyrethrum, pyridaben, pyridalyl, pyridaphenthion, pyridathion, pyrimidifen, pyriprole, pyriproxyfen, quinalphos, resmethrin, RH-5849, ribavirin, RU-12457, RU-15525, rynaxapyr, S-421, S-1833, salithion, sebufos, SI-0009, silafluofen, spinosad, spirodiclofen, spiromesifen, sulfluramid, sulfotep, sulprofos, SZI-121, taufluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogenoxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, *Verticillium lecanii*, WL-108477, WL-40027, yl-5201, yl-5301, yl-5302, XMC, xylylcarb, ZA-3274, zeta-cypermethrin, zolaprofos, ZXI-8901, the compound 3-methylphenyl propylcarbamate (Tsumacide Z), the compound 3-(5-chloro-3-pyridinyl)-8-(2,2,2-trifluoroethyl)-8-azabicyclo[3-.2.1]octane-3-carbonitrile (CAS-Reg. No. 185982-80-3) and the corresponding 3-endo-isomer (CAS-Reg. No. 185984-60-5) (cf. WO-96/37494, WO-98/25923), and also preparations which comprise insecticidally active plant extracts, nematodes, fungi or viruses.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

As used herein, "storage stable" means that the gibberellin does not settle out of the formulation after storage at room temperature or at 40 degrees Celsius for thirty days.

The following examples are intended to illustrate the present invention and to teach one of ordinary skill in the art how to make the formulations of the invention. They are not intended to be limiting in any way.

EXAMPLES

The following commercial products were the sources of the adjuvants in the examples.

Induce® (available from Helena Chemical Company, Collierville, Tenn.; Induce is a registered trademark of Helena Chemical Company) is a surfactant that contains 90% of a blend of alkyl aryl polyoxylkane ethers, dimethylsiloxane, and free fatty acids.

Activator 90 (available from Loveland Products, Inc., Greeley, Colo.) is a nonionic surfactant that contains 90% of a blend of alkylphenol ethoxylate, alcohol ethoxylate and tall oil fatty acid.

Dyne-Amic® (available from Helena Chemical Company, Collierville, Tenn.; Dyne-Amic is a registered trademark of Helena Chemical Company) is a surfactant that contains 99% of a blend of methyl esters of C16 to C18 fatty acids, polyalkyleneoxide and modified polydimethylsiloxane, and alkylphenolethoxylate.

Kinetic® (available from Helena Chemical Company, Collierville, Tenn.; Kinetic is a registered trademark of Helena Chemical Company) is a surfactant that contains 99% of a blend of polyalkyleneoxide modified polydimethylsiloxane and nonionic surfactants.

Example 1

Preparation of Formulations

Applicants used $GA_3$ in the form of Technical Grade Active Ingredient ("TGAI") when preparing formulations of the present invention. The percent $GA_3$ was about 90% w/w. Variations in the amount of $GA_3$ in the TGAI can be accounted for by decreasing or increasing the amount of diluent in order to produce the desired percent of $GA_3$ in the formulation. This is standard practice within the guidelines of U.S. Environmental Protection Agency per 40 C.F.R. § 158.175(b)(2).

The formulations were prepared by adding $GA_3$ TGAI to a sufficient amount of adjuvant to prepare a formulation with a concentration of 0.0216 grams of $GA_3$ per milliliter. The formulations were stirred to complete (or attempt) proper dissolution of the $GA_3$ TGAI.

Four different adjuvants were used to prepare the formulations. The adjuvants contained the following blends of ingredients: (A) 90% of alkyl aryl polyoxyalkane ethers, dimethylsiloxane, and free fatty acids; (B) 90% of alkylphenol ethoxylate, alcohol ethoxylate and tall oil fatty acid; (C) 99% of methyl esters of C16-C18 fatty acids, polyalkyleneoxide and modified polydimethylsiloxane, and alkylphenolethoxylate; and (D) 99% of polyalkyleneoxide modified polydimethylsiloxane and nonionic surfactants. The remaining 1 to 10 percent of the adjuvants are components that are ineffective as adjuvants and proprietary and, accordingly, cannot be described herein.

After stirring the formulations, the following observations were made about the formulations:

(A) the formulation containing 90% of alkyl aryl polyoxyalkane ethers, dimethylsiloxane, and free fatty acids was clear;

(B) the formulation containing 90% of alkylphenol ethoxylate, alcohol ethoxylate and tall oil fatty acid was turbid;

(C) the formulation containing 99% of methyl esters of C16-C18 fatty acids, polyalkyleneoxide and modified polydimethylsiloxane, and alkylphenolethoxylate was separated; and (D) the formulation containing 99% of polyalkyleneoxide modified polydimethylsiloxane and nonionic surfactants was separated.

It was unexpectedly found that a gibberellin formulation containing an adjuvant comprising 90% of alkyl aryl polyoxyalkane ethers, dimethylsiloxane, and free fatty acids would result in a clear formulation. This was unexpected because other adjuvants with similar components did not result in satisfactory formulations.

Example 2

Stability Tests

The formulation from Example 1 that was clear ("Formulation 1A"), containing 90% of alkyl aryl polyoxyalkane ethers, dimethylsiloxane, and free fatty acids, was subjected to stability testing.

Formulation 1A was stored at room temperature for two weeks and then observed. The formulation was clear and stable.

Formulation 1A was stored at room temperature for thirty days and then observed. The formulation was clear and stable.

Formulation 1A was stored at 40 degrees Celsius for thirty days and then observed. The formulation was clear and stable.

Given the difficulty of formulating gibberellins, it was unexpected that Formulation 1A was initially clear as indicated above in Example 1. It was even more unexpected that the formulation would remain clear during room temperature and high temperature storage for an extended period of time. The formulations of the present invention will provide excellent formulations for agricultural use.

The invention claimed is:

1. A liquid agricultural formulation comprising gibberellic acid (GA3) and an adjuvant, wherein:
   the ratio of gibberellic acid (GA3) to adjuvant is about 1:3.2;
   the adjuvant contains about 90% of a blend of alkyl aryl polyoxyalkane ethers, dimethylsiloxane, and free fatty acids;
   the formulation does not include isopropyl alcohol, propylene glycol, or a polysorbate surfactant; and
   the ratios are expressed in percentage weight of the gibberellin by total volume of the formulation to percentage volume of the adjuvant by total volume of the formulation.

2. A method of regulating plant growth comprising the step of treating a soil or a plant with an effective amount of a liquid agricultural formulation comprising gibberellic acid (GA3) and an adjuvant, wherein:
   the ratio of gibberellic acid (GA3) to adjuvant is about 1:3.2;
   the adjuvant contains about 90% of a blend of alkyl aryl polyoxyalkane ethers, dimethylsiloxane, and free fatty acids;
   the formulation does not include isopropyl alcohol, propylene glycol, or a polysorbate surfactant; and
   the ratios are expressed in percentage weight of the gibberellin by total volume of the formulation to percentage volume of the adjuvant by total volume of the formulation.

* * * * *